United States Patent [19]

Andreescu et al.

[11] Patent Number: 4,598,074

[45] Date of Patent: Jul. 1, 1986

[54] β-LACTAM ANTIBIOTICS

[75] Inventors: George Andreescu, Middlesex; Dennis E. Clark, Basking Ridge; William J. Kerr, Somerville, all of N.J.

[73] Assignee: Beecham Group P.L.C., England

[21] Appl. No.: 490,441

[22] Filed: May 2, 1983

Related U.S. Application Data

[63] Continuation-in-part of Ser. No. 434,704, Oct. 15, 1982, abandoned.

[51] Int. Cl.⁴ .................. A61K 31/43; C07D 499/14
[52] U.S. Cl. .................................. 514/196; 260/239.1
[58] Field of Search ............... 424/271; 260/239.1; 374/196

[56] References Cited

U.S. PATENT DOCUMENTS 4,081,546  3/1978  Ferres ............................ 424/271
4,171,303  10/1979  Huhn et al. ................... 260/239.1

FOREIGN PATENT DOCUMENTS 1004670  9/1965  United Kingdom.
1197973  7/1970  United Kingdom.
1312891  4/1973  United Kingdom.
1548405  7/1979  United Kingdom.

OTHER PUBLICATIONS

V. DasGupta et al, "Quantitation of . . . Ticarcillin Disodium by HPLC", J. Pharm. Sci., 69, No. 11, 1264–1267 (Nov. 1980).

Primary Examiner—Natalie Trousof
Assistant Examiner—Vera C. Clarke
Attorney, Agent, or Firm—Jacobs & Jacobs

[57] ABSTRACT

Alpha-carboxy-3-thienylmethyl penicillin having either the R- or the S- configuration at C-10 is obtained in cyrstalline form. The isomers show improved stability and higher biological activity as compared to the amorphous RS material.

15 Claims, 4 Drawing Figures

β-LACTAM ANTIBIOTICS

This is a continuation-in-part of application Ser. No. 434,704 filed Oct. 15, 1982, now abandoned.

This invention relates to β-lactam antibiotics, and more particularly to the penicillin α-carboxy-3-thienylmethyl penicillin.

The penicillin and its salts are active against Gram-positive and Gram-negative bacteria which makes them useful as therapeutic and prophylactic agents against bacterial infections in animals including man.

U.K. Pat. No. 1004670 discloses inter alia α-carboxy-3-thienylmethyl penicillin (ticarcillin) of formula (A) and non-toxic salts thereof:

wherein $R^1$ represents 3-thienyl.

The form in which α-carboxy-3-thienylmethyl penicillin is usually administered is as the disodium salt which is conveniently obtained by dissolving α-carboxy-3-thienylmethyl penicillin in pyrogen-free aqueous sodium alkali at pH 7.5–8.0, filtering the solution and thereafter spray drying or freeze-drying under sterile conditions.

Disodium α-carboxy-3-thienylmethyl penicillin obtained by the processes described above and by any other known process, is prepared as a mixture of diastereoisomers at C-10, i.e. it has the R,S-configuration about the chiral centre in the α-carboxy-3-thienyl methyl side chain. This compound, when obtained by processes such as spray drying is an amorphous hygroscopic product. We have now discovered a process for the production of the separate isomers of α-carboxy-3-thienyl-methyl penicillin having either the R- or the S-configuration at C-10 (hereinafter referred to as R- or S-isomers respectively). The isomers are obtained in crystalline form; the material shows improved stability and higher biological activity over the previously obtained amorphous R,S material.

Accordingly the present invention provides a penicillin salt of formula (I):

which is isomerically enriched with respect to either the R- or S-isomer wherein $M^1$ and $M^2$ are the same or different and each represents a monovalent salt forming cation and $R_1$ represents 3-thienyl.

Suitably the salt is obtained in a pharmaceutically acceptable form, in particular in crystalline form.

The term isomerically enriched when used herein refers to compound containing at least 60% of the chosen isomer (60:40 R:S or S:R), more suitably at least 75% (75:25 R:S or S:R), preferably at least 85% (85:15 R:S or S:R), more preferably at least 95% (95:5 R:S or S:R) and in particular at least 98% of the R- or the S-isomer (98:2 R:S or S:R). The term isomerically enriched includes also the pure (100%) R-isomer and the pure (100%) S-isomer.

The invention therefore provides both the R-isomer of a salt of formula (I) and the S-isomer of a salt of formula (I).

The percentage of the S-isomer and R-isomer in the product may be determined by High Performance Liquid Chromatography (HPLC). One HPLC system which can be used to determine the percentages of the R-isomer and S-isomer is as follows:

Column: μ-Bondapak C-18 (Waters Associates)
Flow rate: 0.7 ml/min
Solvent: 7/93 acetonitrile/aqueous sodium acetate adjusted to pH 6.0 with acetic acid.

Suitably $M^1$ and $M^2$ will be pharmaceutically acceptable cations such as sodium, potassium, ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Preferably $M^1$ and $M^2$ are the same or different and represent sodium or potassium. More preferably $M^1$ and $M^2$ both represent sodium.

One particularly preferred compound within the present invention is R-disodium α-carboxy-3-thienylmethyl penicillin; preferably this is obtained in crystalline form. The crystals are in the shape of elongated prisms. This material preferably contains less than 5% S-isomer, more preferably less than 2% S-isomer, in particular less than 1% S-isomer.

A further particularly preferred compound within the present invention is S-disodium α-carboxy-3-thienylmethyl penicillin; preferably this is obtained in crystalline form. The crystals are in the shape of elongated prisms. This material suitably contains less than 20% R-isomer preferably less than 5% R-isomer, more preferably less than 2% R-isomer, in particular less than 1% R-isomer.

The penicillin salt of this invention is a pharmaceutically useful material and the invention therefore includes within its scope a pharmaceutical composition comprising a penicillin salt of the present invention together with a pharmaceutically acceptable carrier or excipient.

The compositions according to the invention may be formulated for administration in any convenient way for use in human or veterinary medicine, according to techniques and procedures per se known in the art with reference to other antibiotics.

The compositions may be formulated for parenteral administration in the form of liquid preparations, such as sterile parenteral solutions or suspensions.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound may be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Alternatively the compound of the present invention is obtained in a sterile solid form and transferred into vials under sterile conditions. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 25000 mg per day, for instance 18000 or 24000 mg per day depending on the route and frequency of administration.

The penicillin salt according to the present invention may be the sole therapeutic agent in the compositions of the invention or a combination with other antibiotics and/or β-lactamase inhibitor may be employed.

Advantageously the compositions also comprise a β-lactamase inhibitor of formula (II) or a pharmaceutically acceptable salt or ester thereof:

wherein A is hydroxyl, substituted hydroxyl, thiol, substituted thiol, amino, mono- or di-hydrocarbyl substituted amino, or mono- or di-acylamino.

Preferably A is hydroxyl.

A further advantageous composition comprises a penicillin salt according to the invention together with a β-lactamase inhibitor of formula (III) or a pharmaceutically acceptable salt or in vivo hydrolysable ester thereof:

Further suitable β-lactamase inhibitors include 6β-bromopenicillanic acid and salts and in vivo hydrolysable esters and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of a penicillin salt of this invention.

Both the R- and S-isomers of the present invention are active against a broad range of gram positive and gram negative bacteria, in particular they are useful for treatment of respiratory tract and urinary tract infections in humans and mastitis in cattle. The isomers of the present invention are especially valuable in the treatment of Proteus and Pseudomonas infections.

The present invention further provides a process for preparing isomerically enriched α-carboxy-3-thienyl-methyl penicillin of the invention which process comprises allowing crystallisation from a solution in methanol or ethanol of a mixture of isomers of a compound of formula (I) as hereinbefore defined, and thereafter separating the isomerically enriched salt.

There is also provided a process for preparing α-carboxy-3-thienyl-methyl penicillin isomerically enriched with respect to the R-isomer which process comprises allowing preferential crystallisation of the R-isomer from a solution in methanol of a mixture of isomers of a compound of formula (I) as hereinbefore defined, and thereafter separating the isomerically enriched salt.

There is also provided a process for preparing α-carboxy-3-thienyl-methyl penicillin isomerically enriched with respect to the S-isomer which process comprises allowing preferential crystallisation of the S-isomer from a solution in ethanol of a mixture of isomers of a compound of formula (I) as hereinbefore defined, and thereafter separating the isomerically enriched salt.

A mixture of diastereoisomers of formula (I) is dissolved in methanol or ethanol; addition of water is frequently necessary to assist dissolution. The amount of water is suitably kept to a minimum. After the mixture is totally in solution, crystallisation may be allowed by cooling or reducing the polarity of the solution consequently giving precipitation of the resulting crystals. To effect dissolution of the mixture of epimers the solvent can be warmed if necessary. If impurities are present so that all of the solids do not dissolve, the undissolved solids can be removed from the liquid by conventional techniques such as settling, filtration or centrifugation.

The polarity of the solution is suitably reduced by adding a diluent which causes the desired isomer to precipitate.

Suitable diluents will be organic solvents less polar than ethanol, and include $C_{3-10}$ alkanols, $C_{3-10}$ alkanones, di-$C_{1-6}$ alkylethers, $C_{1-6}$ alkyl $C_{1-6}$ alkanoates, $C_{5-12}$ alkanes, cyclic ethers, toluene and benzene.

Preferred diluents include isopropyl ether, acetone, 2-methyl-1-propanol, tetrahydrofuran, dioxan, 1-propanol, toluene, and ligroin.

In general the minimum volume of diluent should be added to cause precipitation. Suitable volumes of diluent to give optimal crystallisation of the R- or S-isomer may be found by trial and error.

Preferably crystallisation of the R- and S-isomers from the methanol or ethanol solution respectively is induced by cooling.

The temperature at which the preparation of solutions and subsequent crystallisation is carried out is not critical, but we have found room temperature to be most convenient. It is, however, useful to cool the solution to ensure complete crystallisation.

It is preferred that the solution should be left to stand for some time before the solid is recovered, and crystallisation may be induced by adding a previously obtained seed crystal.

After the crystals have formed, they can be separated from the supernatant liquid by conventional processes.

These include settling, filtration and centrifugation. The crystals are then suitably dried under mild conditions, for example by placing the material in a desiccator or in a flow of dry air or inert gas. The material is preferably dried to reduce water content to at most 4.5% wt/wt, more preferably at most 2.5% wt/wt.

After separation of the crystals from the supernatant liquid, the solvent is removed from the remaining solute by conventional means, such as evaporation or vacuum evaporation. In some instances, it may be useful to heat the supernatant liquid separated from the crystals to shorten the evaporation time. One of the advantages of the present invention is that the solvent can be recovered from the evaporation step and recycled for further use in the process.

In an advantageous adjunct to the present invention the supernatant liquid, may be stored whereupon spontaneous racemisation occurs; this solution may be used to dissolve further mixture of isomers which may be treated as hereinbefore described to yield, by the process of the present invention, further penicillin salt of the present invention.

At the time the present invention was made it was believed that preferential crystallisation of a mixture of diastereoisomers of formula (I) dissolved in either methanol or ethanol resulted in the enriched R-isomer. It has now been discovered that preferential crystallisaton from the methanol solution results in the enriched R-isomer and that preferential crystallisation from the ethanol solution results in the enriched S-isomer. Thus example 3 below was found to result in production of enriched S-isomers rather than R-isomer as originally believed.

The following Examples illustrate the present invention.

EXAMPLE 1

R-Disodium Ticarcillin

Sodium ethylhexanoate (26.4 g) was dissolved in methanol (100 cm³). Monosodium Ticarcillin (40 g, 100% activity) was added followed by water (10 cm³) to effect complete solution. The solution was stirred at room temperature for 30 minutes and then allowed to stand at room temperature for 30 minutes. When cloudiness occurred the solution was cooled to 0°–5° C. and stored for circa 64 hours. The crystalline precipitate was filtered and washed with isopropyl ether (300 cm³). The wet cake was divided into two portions. Portion A was vacuum dried at 45° C. resulting in 87.0% H.P.L.C. assay. Portion B was air dried at 60° C. resulting in 78.6% H.P.L.C. assay and 7.9% moisture. A total of 27.2 gms. were isolated.

H.P.L.C. system:
Column: μ-Bondapak $C_{18}$ 30 cm × 3.9 mm (Waters)
Flow rate: 0.7 ml/min
Mobile phase: 7/93 acetonitrile/0.05M aqueous sodium acetate adjusted to pH 6.0 with acetic acid
Detector: UV at 254 nm.

EXAMPLE 2

R-Disodium Ticarcillin

Preparation was carried out as in Example 1 but on twice the scale. R-Disodium Ticarcillin (1 g) obtained from Example 1 was used as a seed to induce crystallisation. Vacuum-drying resulted in 62.6 gms. of R-Disodium Ticarcillin with 86.5% assay and 2.3% water.

This represents a yield of 67.7% of R-Disodium Ticarcillin having following properties:

crystal shape . . . elongated prisms which extinguish on rotation in polarised light;
melting point . . . 187°–188° C. with decomposition;
retention time on H.P.L.C. (system as in Example 1) . . . 10 minutes;
$[\alpha]^{20}D$ (1% solution in $H_2O$) . . . +201.6°;
n.m.r. spectrum . . . ($D_2O$); 1.47 (3H, s, $CH_3$), 1.51 (3H, s, $CH_3$), 4.23

(1H, s, N—CH—), 4.66 (1H, s, —CH($CO_2Na$)—) 5.47, 5.56 (2H, q, J=4 Hz,

—CH—CH—), 7.1–7.5 (3H, m, thiophen ring protons);
i.r. spectrum . . . (nujol mull) FIG. 1.

EXAMPLE 3

R-Disodium ticarcillin (i) Crystallisation

Sodium-2-ethylhexanoate (5.4 g) was dissolved in a mixture of methanol (70 ml, analytical reagent grade) and water (2 ml). Monosodium ticarcillin (9.12 g) was added and the clear solution seeded and stored at ca 0° C. for 5 days.

(a) X-Ray diffraction

A sample of the suspension of needle-crystals thus obtained was examined by X-ray diffraction using a Phillips diffractometer and Cu Kα radiation. The following reflections were observed in the range 10 to 30 degrees 2θ.

| 11.1 | 18.8 | 22.2 | 25.8 | 28.6 |
| --- | --- | --- | --- | --- |
| 13.0 | 19.8 | 22.8 | 26.2 | 29.1 |
| 14.9 | 20.2 | 24.7 | 26.8 | 29.5 |
| 16.8 | 20.7 | 24.9 | 27.2 | |
| 17.4 | 21.5 | 25.3 | 27.5 | |

(ii) Isolation and examination of the crystals

The crystals were collected, washed with di-isopropyl ether and dried in vacuum over potassium hydroxide at room temperature.
Yield 6.9 g.

(a) Analysis by nmr

The nmr spectrum ($D_2O$) showed the presence of methanol in the approximate ratio of 2 moles of solvent to 1 mole of penicillin.

(b) X-Ray diffraction

The X-ray diffractogram showed the following reflections in degrees 2θ:

| 11.2 | 19.8 | 22.8 | 26.8 | 29.6 |
| --- | --- | --- | --- | --- |
| 13.1 | 20.2 | 24.8 | 27.2 | |

-continued

| | | | |
|---|---|---|---|
| 15.0 | 20.8 | 25.4 | 27.6 |
| 16.8 | 21.5 | 25.8 | 28.6 |
| 17.5 | 22.3 | 26.2 | 29.1 |
| 18.9 | | | |

(c) Hplc analysis

Analysis by hplc, (using the system, column-Whatman Partisil 5/25 ODS-3, solvent -12/88 methanol /0.1M phosphate buffer at pH 7.0, flow rate—1.5 ml/min) and an integrator, showed the following:

R-epimer, retention time 9.24 mins, 1292800 arbitrary units i.e. 99.2%

S-epimer, retention time 10.91 mins, 10583 arbitrary units, i.e. 0.8%

(iii)

The crystals were dried to constant weight in high vacuum (<0.1 mm Hg) over phosphorous pentoxide at room temperature.

Yield 5.9 g.

The dried product had the following properties:

nmr

Figure 2:
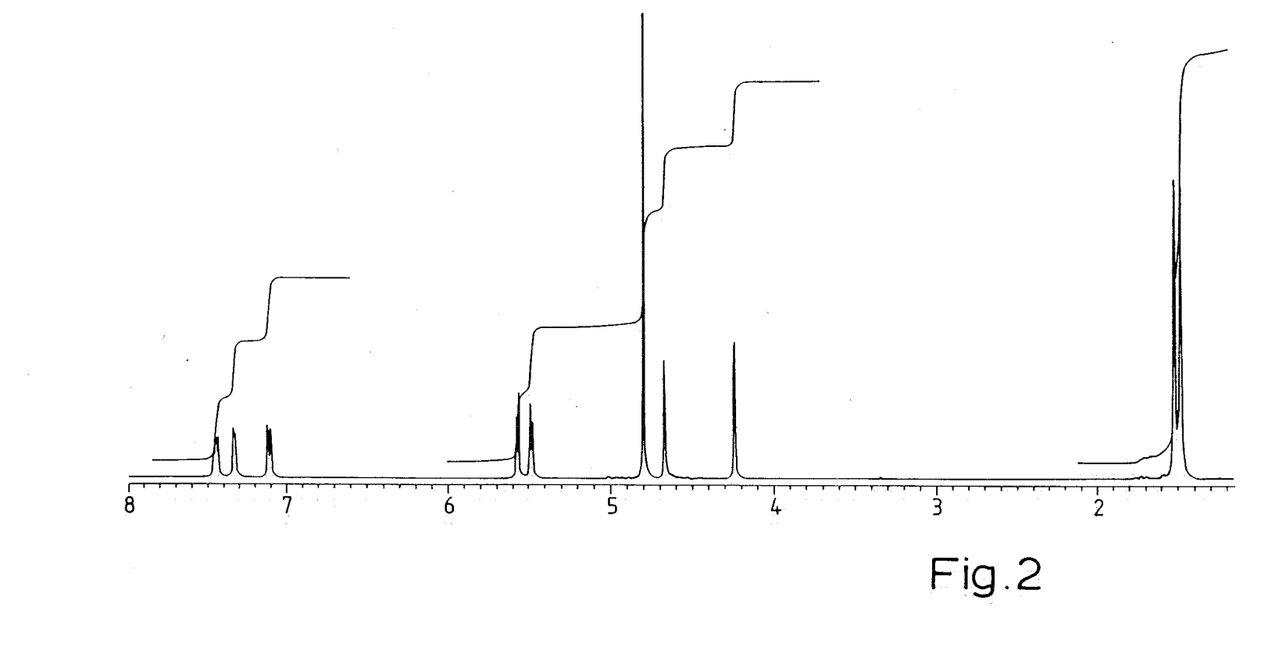

The spectrum (at 250 MHz, ca 4% in $D_2O$) FIG. 2 showed that the methanol had been removed.
1.48 (3H,S,$CH_3$)
1.52 (3H,S,$CH_3$)
4.24 (1H, S, proton at C-3, thiazolidine ring)
4.67 (1H, S, α-proton, side chain)
5.48
5.57 2H,q, J 4 Hz, protons at $C_5$ and $C_6$, β-lactam ring)
7.1–7.5 (3H, m, thiophen ring protons)

epimer ratio (hplc)

Figure 1:
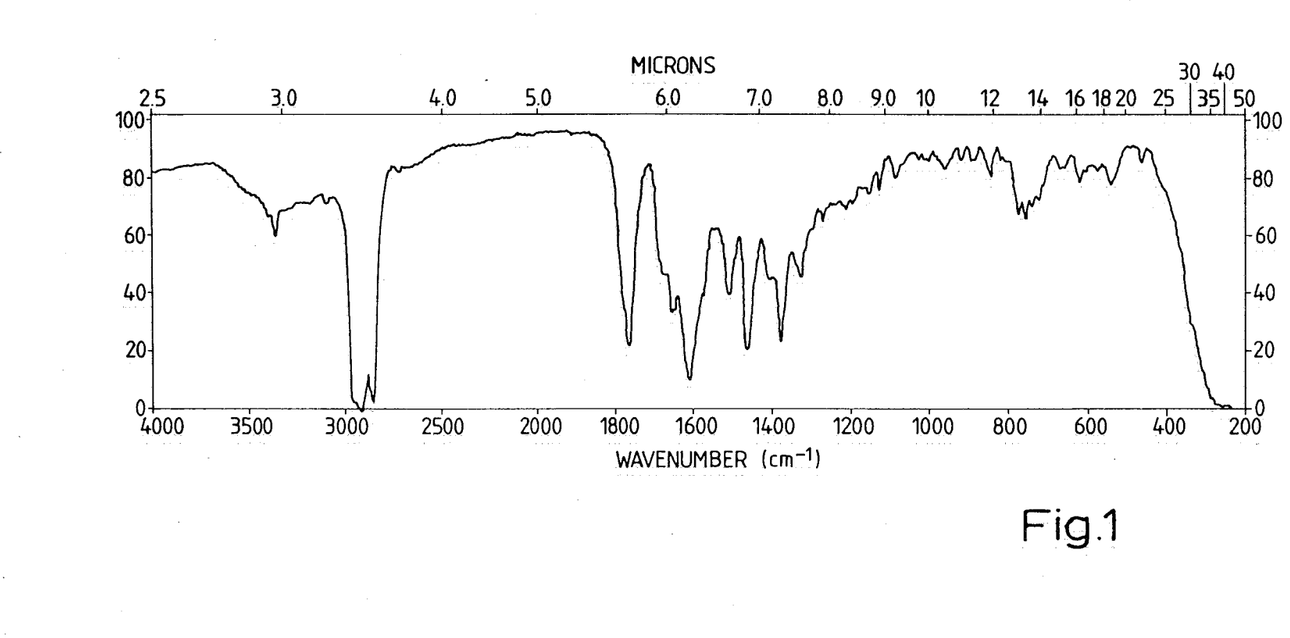

R-epimer 1419900 arbitrary units, i.e. 99.2%
S-epimer 11435 arbitrary units, i.e. 0.8% i.r. spectrum nujol mull—(as FIG. 1).

water 1.75% purity

97% as disodium salt (mercurimetric)

specific rotation $[\alpha]_D^{20}$ +203.9°, 1% in 0.1M phosphate buffer at pH 8.0

EXAMPLE 4

S-Disodium Ticarcillin

Ethanol (300 cm³) was stirred at 15°–20° C. and sodium ethylhexanoate (26.4 g., 1.5 equiv) was added. The mixture was stirred until a clear solution was obtained. It was cooled to 0°–5° C. and Monosodium Ticarcillin (40 g at 100% activity) was added to it in small portions over 15 minutes. It was stirred for 30 minutes when a thick suspension was obtained, water (90 cm³) was added and a clear solution was observed.

To the above solution ethanol (650 ml) was added dropwise over 30 minutes. The precipitated solid was stirred for 90 minutes, filtered, washed with isopropylether and dried under vacuum at 45° C. with nitrogen bleed to yield 36.5 g, (76.5% yield) containing 1.1% water.

EXAMPLE 5

S-Disodium Ticarcillin (i) Crystallisation

Sodium 2-ethyl-hexanoate (2.7 g) was dissolved in a mixture of absolute ethanol (30 ml) and water 9 ml) at room temperature. Monosodium ticarcillin (4.56 g) was added, followed by ethanol (65 ml) and the clear solution left to crystallise for 3 hours at room temperature.

(a) X-ray diffraction

A sample of the suspension of needle-crystals was examined by X-ray diffraction. The following reflections were observed in degrees 2θ:

| | | | | |
|---|---|---|---|---|
| 10.0 | 16.0 | 18.9 | 21.9 | 26.3 |
| 12.8 | 16.7 | 19.5 | 22.2 | 28.1 |
| 13.5 | 16.9 | 19.8 | 22.8 | 28.7 |
| 14.2 | 17.3 | 20.4 | 24.8 | 29.7 |
| 15.8 | 18.5 | 20.9 | 25.7 | |

(ii) Isolation and examination of the crystals

The remaining product was collected, washed with ethanol then di-isopropyl ether and dried in vacuum over calcium chloride at room temperature.

Yield 3.7 g.

(a) X-ray diffraction

The following reflections were observed:

| | | | | |
|---|---|---|---|---|
| 10.0 | 16.0 | 19.8 | 22.7 | 28.0 |
| 10.6 | 16.9 | 20.4 | 24.8 | 28.7 |
| 12.8 | 18.5 | 21.0 | 25.8 | 29.4 |
| 13.5 | 18.9 | 21.9 | 26.4 | |
| 14.2 | 19.5 | 22.3 | 27.0 | |

(b) Epimer ratio

Hplc analysis indicated an approximate ratio of 84% S, 16% R.

(iii) Recrystallisation

Material prepared by the above method was recrystallised as follows:

The enriched S-epimer (12 g) was dissolved in a mixture of absolute ethanol (120 ml) and water (35 ml) and diluted with ethanol (230 ml). The mixture was allowed to crystallise for 1 hour at room temperature, then left at ca 0° C. overnight. The product was collected, washed with ethanol, then di-isopropyl ether, and dried in high vacuum over potassium hydroxide at room temperature.

Yield 8.0 g.

(a) Analysis by nmr

The nmr spectrum showed the presence of approximately 1 mole of ethanol per mole of penicillin.

(b) Analysis by hplc (using the system of Example 3)

Hplc analysis showed the following ratio:
S-epimer, 1436100 arbitrary units, i.e. 97.8%
R-epimer 32454 arbitrary units, i.e. 2.2%

(c) X-ray diffraction

The following reflections were observed:

| | | | | | |
|---|---|---|---|---|---|
| 10.1 | 15.9 | 18.7 | 20.8 | 22.4 | 25.0 |
| 10.8 | 16.2 | 19.0 | 21.1 | 22.8 | 25.9 |
| 12.9 | 16.4 | 19.7 | 21.5 | 23.1 | 27.1 |
| 13.6 | 16.7 | 20.0 | 22.0 | 23.4 | 28.1 |
| 14.4 | 17.4 | 20.5 | 22.2 | 24.4 | 28.8 |
| | | | | 24.7 | 29.7 |

(iv)

The crystals were dried to constant weight in high vacuum over phosphorous pentoxide at room temperature.

Yield 7.2 g.

The dried product had the following properties:

nmr

Figure 3:
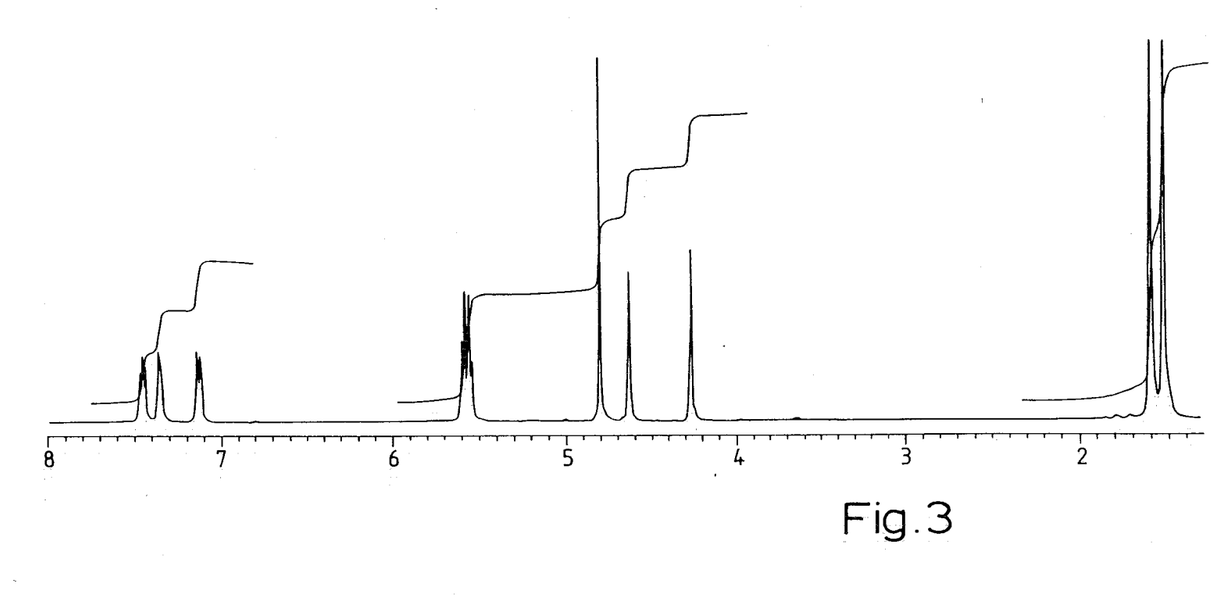

The nmr spectrum (at 250 MHz, ca 4% in $D_2O$) FIG. 3 showed that the ethanol had been removed.

1.52 (3H, S, $CH_3$)
1.60 (3H, S, $CH_3$)
4.27 (1H, S, proton at C-3, thiazolidine ring)
4.63 (1H, S, α-proton of side chain)
(5.55)
(5.59) (2H, q, J 4 Hz, protons at $C_5$ and $C_6$, β-lactam ring)
7.1–7.5 (3H, m, thiophen ring protons)

epimer ratio (hplc)

S-epimer 1525900 arbitrary units, i.e. 97.9%
R-epimer 32790 arbitrary units, i.e. 2.1% i.r. spectrum

Figure 4:
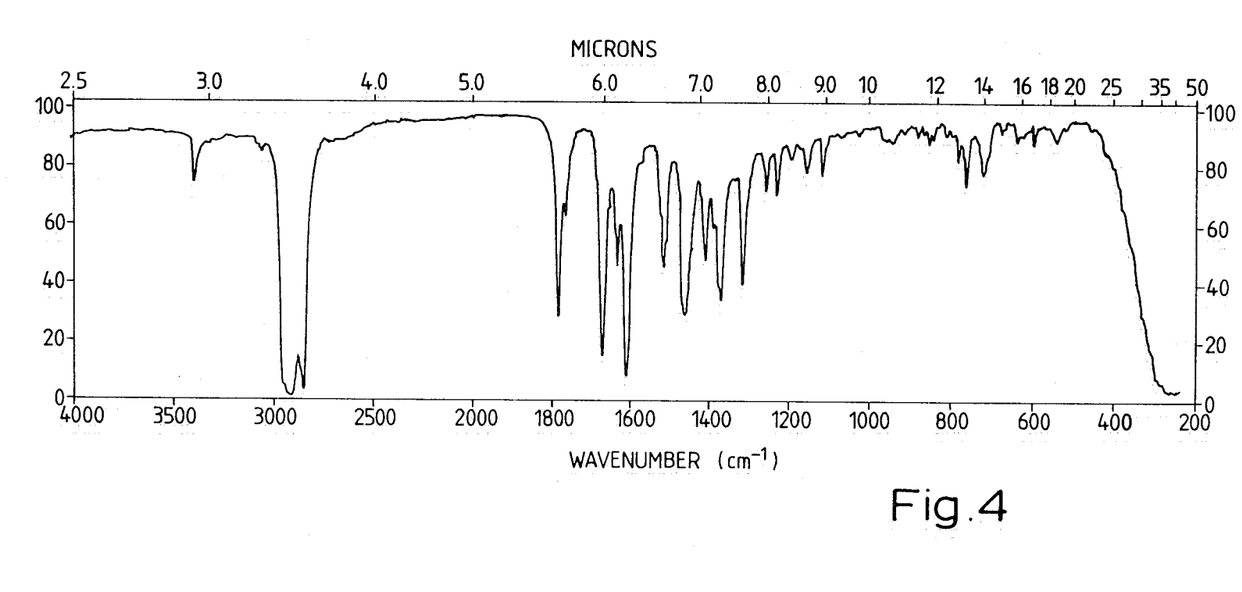

Nujol mull—FIG. 4 water 0.4% purity 97.0% as disodium salt (mercurimetric)

specific rotation $[\alpha]_D^{20} + 160.3°$, 1% in 0.1M phosphate buffer at pH 8.0.

(v) A sample (200 mg) of Ticarcillin S-epimer (epimeric purity ca. 98%) was recrystallised from water (0.5 ml) and ethanol (5.0 ml). The product was shown by hplc analysis to be of greater than 99% epimeric purity.

We claim:

1. A process for preparing a penicillin salt selected from the group consisting of a salt of the Formula (I):

wherein $M^1$ and $M^2$ are the same or different and each is a monovalent salt forming cation, and $R^1$ is 3-thienyl at least 60% of which has the R-configuration at C-10 and such a salt at least 60% of which has the S-configuration at C-10 which comprises allowing crystalization from a solution in methanol or ethanol as appropriate of a mixture the R- and S-isomers and thereafter separating the R- or S-isomer.

2. A process according to claim 1 wherein crystallisation of the R-isomer from methanol is induced by cooling.

3. A process according to claim 1 wherein crystallisation of the S-isomer from ethanol is induced by cooling.

4. A pharmaceutical composition useful for treating bacterial infections in humans and animals which comprises a β-lactamase inhibitory amount of a β-lactamase inhibitor and an antibacterially effective amount of a penicillin salt selected from the group consisting of a salt of the Formula (I):

wherein $M^1$ and $M^2$ are the same or different and each is a monovalent salt forming cation, and $R^1$ is 3-thienyl, at least 60% of which has the R-configuration at C-10 and such a salt at least 60% of which has the S-configuration at C-10 in combination with a pharmaceutically acceptable carrier.

5. A composition according to claim 4 wherein the penicillin salt is a salt at least 98% of which has the R-configuration at C-10.

6. A composition according to claim 4 wherein the penicillin salt is a salt at least 98% of which has the S-configuration at C-10.

7. A composition according to claim 4 wherein $M^1$ and $M^2$ are the same or different and each is sodium or potassium.

8. A composition according to claim 4 wherein the penicillin salt is R-disodium α-carboxy-3-thienylmethyl penicillin.

9. A composition according to claim 4 wherein the penicillin salt is S-disodium α-carboxy-3-thienylmethyl penicillin.

10. A method of treating bacterial infections in humans and animals which comprises administering to a human or animal in need thereof a β-lactamase inhibitory amount of a β-lactamase inhibitor and an antibacterially effective amount of a penicillin salt selected from the group consisting of a salt of the Formula (I):

wherein $M^1$ and $M^2$ are the same or different and each is a monovalent salt forming cation, and $R^1$ is 3-thienyl, at least 60% of which has the R-configuration at C-10 and such a salt at least 60% of which has the S-configuration at C-10 in combination with a pharmaceutically acceptable carrier.

11. A method according to claim 10 wherein the penicillin salt is a salt at least 98% of which has the R-configuration at C-10.

12. A method according to claim 10 wherein the penicillin salt is a salt at least 98% of which has the S-configuration at C-10.

13. A method according to claim 10 wherein $M^1$ and $M^2$ are the same or different and each is sodium or potassium.

14. A method according to claim 10 wherein the penicillin salt is R-disodium -carboxy-3-thienylmethyl penicillin.

15. A method according to claim 10 wherein the penicillin salt is S-disodium -carboxy-3-thienylmethyl penicillin.

* * * * *

UNITED STATES PATENT AND TRADEMARK OFFICE
CERTIFICATE OF CORRECTION

PATENT NO. : 4,598,074
DATED : July 1, 1986
INVENTOR(S) : GEORGE ANDREESCU ET AL It is certified that error appears in the above-identified patent and that said Letters Patent are hereby corrected as shown below:

CLAIMS 14 AND 15, LINE 2

Kindly insert "$\alpha$" preceding "-carboxy".

Signed and Sealed this

Twenty-eighth Day of October, 1986

[SEAL]

Attest:

DONALD J. QUIGG

Attesting Officer     Commissioner of Patents and Trademarks